US006566363B2

(12) United States Patent
Chong et al.

(10) Patent No.: US 6,566,363 B2
(45) Date of Patent: May 20, 2003

(54) PYRAZOLE-THIAZOLE COMPOUNDS, PHARMACEUTICAL COMPOSITIONS CONTAINING THEM

(75) Inventors: Wesley Kwan Mung Chong, Encinitas, CA (US); Rohit Kumar Duvadie, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/923,432

(22) Filed: Aug. 8, 2001

(65) Prior Publication Data

US 2002/0049215 A1 Apr. 25, 2002

Related U.S. Application Data

(60) Provisional application No. 60/223,989, filed on Aug. 9, 2000.

(51) Int. Cl.[7] ................... A61K 31/429; A61K 31/496; C07D 513/04

(52) U.S. Cl. .................. 514/254.04; 514/367; 544/367; 544/368; 548/153

(58) Field of Search .......................... 548/153; 544/367, 544/368; 514/367, 254.04

(56) References Cited

U.S. PATENT DOCUMENTS

| | | | |
|---|---|---|---|
| 5,621,082 | A | 4/1997 | Xiong et al. |
| 5,733,920 | A | 3/1998 | Mansuri et al. |
| 5,922,741 | A | 7/1999 | Davis et al. |

FOREIGN PATENT DOCUMENTS

| | | |
|---|---|---|
| DE | 2429195 | 2/1976 |
| EP | 0666270 A2 | 9/1995 |
| WO | WO96/14843 | 5/1996 |
| WO | WO97/16447 | 9/1997 |
| WO | WO97/40019 | 10/1997 |
| WO | WO97/42949 | 11/1997 |
| WO | WO98/08486 | 3/1998 |
| WO | WO98/17662 | 4/1998 |
| WO | WO98/33798 | 8/1998 |
| WO | WO99/02162 | 1/1999 |
| WO | WO99/06540 | 2/1999 |
| WO | WO99/15500 | 4/1999 |
| WO | WO99/17769 | 4/1999 |
| WO | WO99/21845 | 5/1999 |
| WO | WO 99/21845 A2 * | 5/1999 |
| WO | WO99/24416 | 5/1999 |
| WO | WO99/43675 | 9/1999 |
| WO | WO99/43676 | 9/1999 |
| WO | WO99/54308 | 10/1999 |
| WO | WO99/62890 | 12/1999 |

OTHER PUBLICATIONS

Pawar et al., CA 112:158124, 1990.*
Chande et al., Indian J. Chem. Sect. B, 34(11), (1995), pp. 985–989.*
Chemical Abstracts, vol. 90, No. 25 (1979), Abstract No. 203972z.
Chemical Abstracts, vol. 112, No. 17 (1990), Abstract No. 158124j.
Chemical Abstracts, vol. 124, No. 21 (1996), Abstract No. 289343a.
International Search Report, PCT/US 01/41466, Jul. 31, 2001.
Ann. Rev. Cell Dev. Biol. 13, 261–291 (1997).
Bagshawe, Drug Dev. Res. 34, 220–230 (1995).
Bandara et al., Nature Biotech. 15, 896–901 (1997).
Bertolini et al., J. Med. Chem. 40, 2011–2016 (1997).
Bodor, Advances in Drug Res. 13, 255–331 (1984).
Bundgaard, Design of Prodrugs (Elsevier Press), (1985), Table of Contents and Title Pages Only.
Chang et al., Chemistry and Biology 6, 361–375 (1999).
Chen et al., Proc. Natl. Acad. Sci. USA 96, 4325–4329 (1999).
Cohen et al., Proc. Natl. Acad. Sci. USA 95, 14272–14277 (1998).
Del Sal et al., Critical Rev. Oncogenesis 7(1&2), 127–142 (1996).
Grant et al., Proc. Amer. Assoc. Cancer Res. 39, Abst. 1207 (1998).
Gray et al., Science 281, 533–538 (1998).
Hall and Peters, Adv. Cancer Res. 68, 67–108 (1996).
Harper, Cancer Surv. 29, 91–107 (1997).
Ismail et al., Chem. Papers 51, 43–47 (1997).
Jeffrey et al., Mechanism of CDK activation revealed by the structure of a cyclin A–CDK2 complex, Nature 376, 313–320 (Jul. 27, 1995).
Kamb et al., Science 264, 436–440 (1994).
Krogsgaard–Larsen et al., eds., Drug Design and Development, Design and Application of Prodrugs, Harwood Academic Publishers, (1991), Table of Contents and Title Pages Only.
Lee et al., Biochem. 23, 4255–4261 (1984).
Legraverend et al., Bioorg. Med. Chem. Lett. 8, 793–798 (1998).
Loda et al., Nature Medicine 3, 231–234 (1997).
Lukas et al., Genes and Dev. 11, 1479–1492 (1997).

(List continued on next page.)

Primary Examiner—Laura L. Stockton
(74) Attorney, Agent, or Firm—Bryan C. Zielinski; Joseph Reidy; Wendy Lei Hsu

(57) ABSTRACT

Pyrazole-thiazole compounds that modulate and/or inhibit the activity of cyclin-dependent kinases are described. These compounds and pharmaceutical compositions containing them are capable of mediating cyclin-dependent diseases to modulate and/or inhibit unwanted cell proliferation. The invention is also directed to the therapeutic or prophylactic use of pharmaceutical compositions containing such compounds, and to methods of treating cancer as well as other disease states associated with unwanted angiogenesis and/or cellular proliferation, such as diabetic retinopathy, glaucoma, rheumatoid arthritis, and psoriasis, by administering effective amounts of such compounds.

9 Claims, No Drawings

OTHER PUBLICATIONS

Luzzio et al., *Proc. Amer. Assoc. Cancer Res.*, Abst. 4102 (1999).
Meijer and Kim, Chemical Inhibitors of Cyclin–Dependent Kinases, *Methods in Enzymol* 283, 113–128 (1997).
Meyer et al., *Proc. Amer. Assoc. Cancer Res.* 39, Abst. 3794 (1998).
Mossman, *Journal of Immunological Methods* 65, 55–63 (1983).
Nobori et al., *Nature* 368, 753–756 (1994).
Owa et al., *J. Med. Chem.* 42, 3789–3799 (1999).
Rosenblatt et al., Purification and Crystallization of Human Cyclin–Dependent Kinase 2, *J. Mol. Biol.* 230, 1317–1319 (1993).
Ruetz et al., *Proc. Amer. Assoc. Cancer Res.* 39, Abst. 3796 (1998).
Schow et al., *Bioorg. Med. Chem. Lett.* 7, 2697–2702 (1997).
*Science* 274, 1643–1677 (1996).
Schultz et al., *J. Med. Chem.*, 2909–2919 (1999).
Sedlacek et al., *Int. J. Oncol.* 9, 1143–1168 (1996).
Seitz et al., $218^{th}$ *ACS Natl. Mtg.* Abst. MEDI 316 (Aug. 22–26, 1999), New Orleans).
Shan et al., *J. Pharm. Sci.* vol. 86, No. 7, 765–767 (1997).
Sherr et al., *Genes Dev.* 13, 1501–1512 (1999).
Singh, R.V.K. et al., *J. Ind. Chem. Soc.* 68, 167–168 (1991).
Singh, R.V.K. et al., *J. Inst. Chem.* (*India*) 64, 55–58 (1992).
Sjogren et al., *J. Med. Chem.* 34, 3295–3301 (1991).
Still et al., *J. Org. Chem.* 43, 2923–2925 (1978).
Stover et al., *Curr. Opin. in Drug disc. and Devel.* 2, 274–285 (1999).
Webster, *Exp. Opin. Invest. Drugs* 7, 865–887 (1998).

* cited by examiner

PYRAZOLE-THIAZOLE COMPOUNDS, PHARMACEUTICAL COMPOSITIONS CONTAINING THEM

RELATED APPLICATION DATA

This application claims priority to U.S. Provisional Patent Application Ser. No. 60/223,989, filed Aug. 9, 2000.

TECHNICAL FIELD AND INDUSTRIAL APPLICABILITY OF THE INVENTION

This invention is directed to 5-amino-3-substituted-pyrazolo[4,5-d]thiazole compounds that mediate and/or inhibit the activity of cyclin-dependent kinases (CDKs), such as CDK1, CDK2, CDK4, and CDK6, and to pharmaceutical compositions containing such compounds. The invention is also directed to the therapeutic or prophylactic use of such compounds and compositions, and to methods of treating cancer as well as other disease states associated with unwanted angiogenesis and/or cellular proliferation, by administering effective amounts of such compounds.

BACKGROUND OF THE INVENTION

Uncontrolled cell proliferation is the insignia of cancer. Cell proliferation in response to various stimuli is manifested by a deregulation of the cell division cycle, the process by which cells multiply and divide. Tumor cells typically have damage to the genes that directly or indirectly regulate progression through the cell division cycle.

CDKs constitute a class of enzymes playing critical roles in regulating the transitions between different phases of the cell cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occur. See, e.g., the articles compiled in *Science*, vol. 274 (1996), pp. 1643–1677; and *Ann. Rev. Cell Dev. Biol.*, vol. 13 (1997), pp. 261–291. CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

The D cyclins are sensitive to extracellular growth signals and become activated in response to mitogens during the $G_1$ phase of the cell cycle. CDK4/cyclin D plays an important role in cell cycle progression by phosphorylating, and thereby inactivating, the retinoblastoma protein (Rb). Hypophosphorylated Rb binds to a family of transcriptional regulators, but upon hyperphosphorylation of Rb by CDK4/cyclin D, these transcription factors are released to activate genes whose products are responsible for S phase progression. Rb phosphorylation and inactivation by CDK4/cyclin D permit passage of the cell beyond the restriction point of the $G_1$ phase, whereupon sensitivity to extracellular growth or inhibitory signals is lost and the cell is committed to cell division. During late $G_1$, Rb is also phosphorylated and inactivated by CDK2/cyclin E, and recent evidence indicates that CDK2/cyclin E can also regulate progression into S phase through a parallel pathway that is independent of Rb phosphorylation (see Lukas et al., *Genes and Dev.*, vol. 11 (1997), pp. 1479–1492).

The progression from $G_1$ to S phase, accomplished by the action of CDK4/cyclin D and CDK2/cyclin E, is subject to a variety of growth regulatory mechanisms, both negative and positive. Growth stimuli, such as mitogens, cause increased synthesis of cyclin D1 and thus increased functional CDK4. By contrast, cell growth can be down regulated in response to DNA damage or negative growth stimuli, by the induction of endogenous inhibitory proteins. These naturally occurring protein inhibitors include $p21^{WAF1/CIP1}$, $p27^{KIP1}$, and the $p16^{INK4}$ family, the latter of which inhibit CDK4 exclusively (see Harper, *Cancer Surv.*, vol. 29 (1997), pp. 91–107). Aberrations in this control system, particularly those that affect the function of CDK4 and CDK2, are implicated in the advancement of cells to the highly proliferative state characteristic of malignancies, such as familial melanomas, esophageal carcinomas, and pancreatic cancers (see, e.g., Hall and Peters, *Adv. Cancer Res.*, vol. 68 (1996), pp. 67–108; and Kamb et al., *Science*, vol. 264 (1994), pp. 436–440). Over-expression of cyclin D1 is linked to esophageal, breast, and squamous cell carcinomas (see, e.g., Del Sal et al., *Critical Rev. Oncogenesis*, vol. 71 (1996), pp. 127–142). Genes encoding the CDK4-specific inhibitors of the p16 family frequently have deletions and mutations in familial melanoma, gliomas, leukemias, sarcomas, and pancreatic, non-small cell lung, and head and neck carcinomas (see Nobori et al., *Nature*, vol. 368 (1994), pp. 753–756).

Amplification and/or overexpression of cyclin E has also been observed in a wide variety of solid tumors, and elevated cyclin E levels have been correlated with poor prognosis. In addition, the cellular levels of the CDK inhibitor p27, which acts as both a substrate and inhibitor of CDK2/cyclin E, are abnormally low in breast, colon, and prostate cancers, and the expression levels of p27 are inversely correlated with the stage of disease (see Loda et al., *Nature Medicine*, vol. 3 (1997), pp. 231–234). Recently there is evidence that CDK4/cyclin D might sequester p27, as reviewed in Sherr et al., *Genes Dev.*, vol. 13 (1999), pp. 1501–1512. The p21 proteins also appear to transmit the p53 tumor-suppression signal to the CDKs; thus, the mutation of p53 in approximately half of all human cancers may indirectly result in deregulation of CDK activity.

Inhibitors of CDKs, and CDK4 and CDK2 in particular, are useful as anti-proliferative therapeutic agents. Certain biomolecules have been proposed for this purpose. For example, U.S. Pat. No. 5,621,082 to Xiong et al. discloses nucleic acid which encode for inhibitors of CDK6, and International Publication No. WO 99/06540 discloses inhibitors for CDKs as well. Peptides and peptidomimetic inhibitors are also described in: European Patent Publication No. 0 666 270 A2; Bandara et al., *Nature Biotech.*, vol. 15 (1997), pp. 896–901; and Chen et al., *Proc. Natl. Acad. Sci. USA*, vol. 96 (1999), pp. 4325–4329. Peptide aptamers are identified in Cohen et al., *Proc. Natl. Acad. Sci. USA*, vol. 95 (1998), pp. 14272–14277, and several small molecules have been recently identified as CDK inhibitors (for recent reviews, see Webster, *Exp. Opin. Invest. Drugs*, vol. 7 (1998), pp. 865–887, and Stover et al., *Curr. Opin. in Drug Disc. and Devel.*, vol. 2 (1999), pp. 274–285).

The flavone, flavopiridol, displays modest selectivity for inhibition of CDKs over other kinases, but inhibits CDK4, CDK2, and CDK1 equipotently, with $IC_{50}$s in the 0.1–0.3 $\mu$M range. Flavopiridol is currently in clinical trials as an oncology chemotherapeutic (Sedlacek et al., *Int. J. Oncol.*, vol. 9 (1996), pp. 1143–1168). Analogs of flavopiridol are the subject of other publications, for example, U.S. Pat. No. 5,733,920 to Mansuri et al. (see also International Publication No. WO 97/16447) and International Publication Nos. WO 97/42949 and WO 98/17662. Results of inhibition of CDKs with purine-based derivatives are described in: Schow et al., *Bioorg. Med. Chem. Lett.*, vol. 7 (1997), pp. 2697–2702; Grant et al., *Proc. Amer. Assoc. Cancer Res*,. vol. 39 (1998), Abst. 1207; Legravend et al., *Bioorg. Med. Chem. Lett.*, vol. 8 (1998), pp. 793–798; Gray et al., *Science*, vol. 281 (1998), pp. 533–538; Chang, et al., *Chemistry & Biology*, vol. 6 (1999), pp. 361–375; and International Publication Nos. WO 99/02162, WO 99/43675, and WO 99/43676.

In addition, the following publications disclose certain pyrimidines that inhibit cyclin-dependent kinases and growth-factor mediated kinases: International Publication No. WO 98/33798; Ruetz et al., *Proc. Amer. Assoc. Cancer Res*,. vol. 39 (1998), Abst. 3796; and Meyer et al., *Proc. Amer. Assoc. Cancer Res.*, vol. 39 (1998), Abst. 3794. Certain benzensulfonamides that block cells in G1 are described in Owa et al., *J. Med. Chem.*, vol. 42 (1999), pp. 3789–3799. An oxindole CDK inhibitor is described in Luzzio et al., *Proc. Amer. Assoc. Cancer Res.* (1999), Abst. 4102, and International Publication No. WO 99/15500. Paullones have also been described by Schultz et al., *J. Med. Chem.* (1999), pp. 2909–2919. Indenopyrazoles are described in International Publication No. WO 99/17769 and by Seitz et al, $218^{th}$ *ACS Natl. Mtg.* (Aug. 22–26, 1999, New Orleans), Abst. MEDI 316. Aminothiazoles are described in International Publication Nos. WO 99/24416 and WO 99/21845. Isothiazole derivatives are described in WIPO Publication No. WO 99/6280. Pyrazole inhibitors of protein kinases are described in WIPO Publication No. WO 96/14843. Pyrazole-4-one analogs are described in WIPO Publication No. WO 99/54308. 5-Aminopyrazole as inhibitors of protein tyrosine kinase p56 1ck are described in WIPO Publication No. WO 97/40019.

A few examples of pyrazole-thiazole ring systems are known in the art. For example Singh et al. describe the 3-alkyl-5-alkylamino tautomer, phenyl-(3-phenyl-2,6,-dihydro-pyrazolo[3,4-d]thiazol-5-ylidene)-amine, shown below as Example 1 (see Singh, R. V. K. et al., *J. Ind. Chem. Soc.*, vol. 68, pp. 167–168 (1991) and Singh, R. V. K., *J. Inst. Chem. (India)*, vol. 64, pp. 55–58 (1992)). 5-acylamino substituents are described by Eilingsfeld, H. et al. in German Patent Publication DE 2429195 (Jun. 18, 1974). 3,3a-dihydro-pyrazolo[4,5-d]-thiazoles are described by Ismail et al. (Chem. Papers, vol. 51, pp. 43–47 (1997)) and shown below as Example 2.

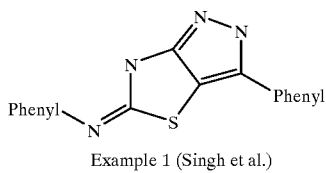

Example 1 (Singh et al.)

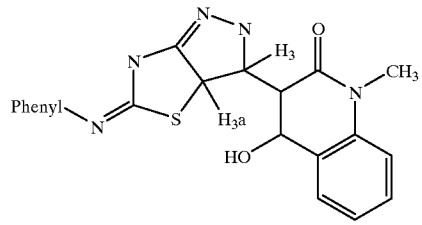

Example 2 (Ismail et al.)

The above publications do not describe these compounds as cyclin or CDK inhibitors.

Thus, there is still a need, however, for other small-molecule compounds that may be readily synthesized and are potent inhibitors of one or more CDKs or CDK/cyclin complexes. Because CDK4 may serve as a general activator of cell division in most cells, and because complexes of CDK4/cyclin D and CDK2/cyclin E govern the early $G_1$ phase of the cell cycle, there is a need for effective and specific inhibitors of CDK4 and/or CDK2 for treating one or more types of tumors.

SUMMARY OF THE INVENTION

Accordingly, one object of the invention is to attain compounds and drug compositions that inhibit the activity of one or more CDKs, such as CDK2, CDK4, and/or CDK6, or cyclin complexes thereof. A further object is to provide an effective method of treating cancer indications through CDK inhibition, preferably selectively, such as through inhibition of CDK4 or CDK4/D-type cyclin complexes and/or CDK2 or CDK2/E-type cyclin complexes. Another object is to achieve pharmaceutical compositions containing compounds effective to block the transition of cancer cells into their proliferative phase. These and other objects and advantages of the invention, will become apparent in light of the detailed description and through the practice of the invention and its various embodiments.

In one general aspect, the present invention is directed to cell-cycle control agents that are compounds of the Formula I:

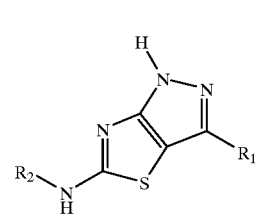

(I)

wherein:
$R_1$ is a substituted or unsubstituted alkyl, aryl, heteroaryl, cycloalkyl, or heterocycloalkyl group; and
$R_2$ is a substituted or unsubstituted alkyl, aryl, heteroaryl, cycloalkyl, or heterocycloalkyl group, with the proviso that $R_1$ and
$R_2$ may not both be an unsubstituted phenyl;
or pharmaceutically acceptable salts, multimeric forms, prodrugs, or pharmacologically active metabolites thereof or pharmaceutically acceptable salts of such metabolites.

In another general aspect, the present invention is directed to cell-cycle control agents of the Formula II:

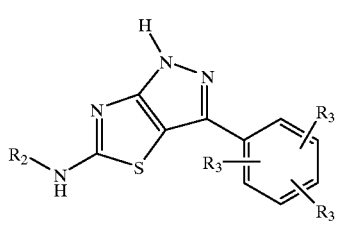

(II)

wherein:
$R_2$ is as defined above; and
each $R_3$ is independently hydrogen or halogen, or a substituted or unsubstituted alkyl, aryl, heteroaryl, cycloalkyl, or heterocycloalkyl group, with the proviso that if $R_2$ is an unsubstituted phenyl then all $R_3$ may not be hydrogen;

or pharmaceutically acceptable salts, multimeric forms, prodrugs, or pharmacologically active metabolites thereof or pharmaceutically acceptable salts of such metabolites.

In another general aspect, the present invention is directed to cell-cycle control agents of the Formula IIa:

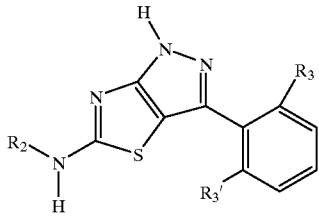

(IIa)

wherein:
$R_2$ and $R_3$ are as defined above; and
$R_3'$ is hydrogen, halogen, or a substituted or unsubstituted alkyl, aryl, heteroaryl, cycloalkyl, or heterocycloalkyl group, with the proviso that if $R_2$ is an unsubstituted phenyl then $R_3$ and $R_3'$ may not both be hydrogen;
or pharmaceutically acceptable salts, multimeric forms, prodrugs, or pharmacologically active metabolites thereof or pharmaceutically acceptable salts of such metabolites.

In another general aspect, the invention is directed to pharmaceutical compositions each comprising:
(a) a cell-cycle control agent selected from compounds of the Formula I below:

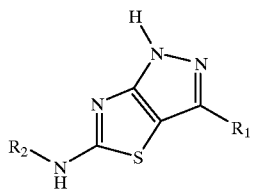

(I)

wherein:
$R_1$ is a substituted or unsubstituted alkyl, aryl, heteroaryl, cycloalkyl, or heterocycloalkyl group; and
$R_2$ is a substituted or unsubstituted alkyl, aryl, heteroaryl, cycloalkyl, or heterocycloalkyl group;
or pharmaceutically acceptable salts, multimeric forms, prodrugs, or pharmacologically active metabolites thereof, or pharmaceutically acceptable salts of such metabolites; and
(b) a pharmaceutically acceptable carrier.

In a further general aspect, the invention provides a method of treating diseases or disorders mediated by CDK inhibition, such as those mediated by CDK4 and/or CDK2 inhibition, by administering to a patient in need of such treatment an effective amount of a cell-cycle control agent of the invention.

The invention further provides a method of treating malignancies or cancers as well as other disease states associated with unwanted angiogenesis and/or cellular proliferation, and mycotic infection, comprising administering an effective amount of a cell-cycle control agent of the invention to a patient in need of such treatment.

The invention also provides a method of modulating and/or inhibiting the kinase activity of a CDK complex by administering a cell-cycle control agent of the invention to a patient. Additionally, the invention is directed to the therapeutic use of the pharmaceutical compositions of the invention in treating diseases mediated by kinase activity, such as cancer as well as other disease states associated with unwanted angiogenesis and/or cellular proliferation, such as diabetic retinopathy, glaucoma, rheumatoid arthritis, restenosis, and psoriasis.

DETAILED DESCRIPTION AND PREFERRED EMBODIMENTS OF THE INVENTION

The term "cell-cycle control agent" as used herein refers to compounds of the invention (e.g., of the Formula I, the Formula II and the Formula IIa), as well as pharmaceutically acceptable salts, multimeric forms, prodrugs, pharmacologically active metabolites of such compounds and pharmaceutically acceptable salts of such metabolites.

The terms "alkyl" and "alkyl group" as used herein refer to saturated or unsaturated, straight—and branched-chains of carbon and hydrogen atoms, preferably having 1 to 14 carbon atoms. Exemplary alkyl groups include methyl, ethyl, n-propyl, isopropyl, butyl, isobutyl, sec-butyl, tert-butyl, pentyl, isopentyl, tert-pentyl, hexyl, isohexyl, and the like. The terms lower alkyl: and "lower alkyl group" refer to alkyls having from 1 to 4 carbon atoms in its chain. The alkyl can be substituted or unsubstituted by one or more substituents defined below. Exemplary substituted alkyl groups include fluoromethyl, difluoromethyl, trifluoromethyl, 2-fluoroethyl, 3-fluoropropyl, hydroxymethyl, 2-hydroxyethyl, 3-hydroxypropyl, and the like. Any suitable alkyl group can be used as $R_1$ and/or $R_2$ and /or $R_3$ and /or $R_3'$.

The terms "cycloalkyl" and "cycloalkyl group" as used herein refer to saturated and unsaturated, monocylic and polycyclic carbon ring structures containing from 3 to 14 carbon atoms Exemplary cycloalkyls include cyclopropyl, cyclobutyl, cyclopentyl, cyclohexyl, cycloheptyl, napthyl and the like. The cycloalkyls may be substituted or unsubstituted by one or more substituents defined below, and to may be fused with one or more heterocycloalkyl groups, aryl groups, or heteroaryl groups, which themselves may be which be substituted or unsubstituted by one or more substituents.

The terms "heterocycloalkyl" and "heterocycloalkyl group" as used herein refer to saturated and unsaturated, monocylic and polycyclic carbon ring structures containing from 3 to 18 ring atoms and including at least one, preferably 1 to 5, heteroatoms selected from nitrogen, oxygen, and sulfur. Exemplary heterocycloalkyls include tetrahydrofuranyl, tetrahydropyranyl, azetidinyl, pyrrolidinyl, piperidinyl, piperazinyl, thiazinyl, morpholinyl, and the like. The heterocycloalkyl may be monocyclic, bicyclic, or tricyclic and may be unsubstituted or substituted by one or more substituents as defined below. The heterocyloalkyl may also be fused with one or more cycloalkyl groups, aryl groups, or heteroaryl groups, which themselves may be unsubstituted or substituted by one or more substituents.

The terms "aryl" and "aryl group" as used herein refer to monocyclic or polycyclic aromatic ring structures containing 6, 10, 14, or 18 carbon ring atoms. The aryl may be unsubstituted or substituted by one or more substituents as defined below, and may be fused with one or more cycloalkyl groups, heterocycloalkyl groups, or heteroaryl groups, which themselves may be unsubstituted or substituted by one or more substituents.

The terms "heteroaryl" and "heteroaryl group" as used herein refer to monocyclic or polycyclic unsaturated or aromatic ring structures containing from 4 to 18 ring atoms, including from 1 to 5 heteroatoms selected from nitrogen, oxygen, and sulfur. The heteroaryl may be unsubstituted or substituted by one or more suitable substituents as defined below, and may be fused with one or more cycloalkyl groups, heterocycloalkyl groups, or aryl groups, which themselves may be unsubstituted or substituted by one or more suitable substituents.

Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzothiophenyl (thianaphthenyl), furanyl, thiophenyl, imidazolyl, oxazolyl, isoxazolyl, thiazolyl, triazolyl, tetrazolyl, isoquinolinyl, acridinyl, pyrimidinyl, benzimidazolyl, benzofuranyl, and the like.

In the context of the present invention, the aryl, heteroaryl, cycloalkyl, and heterocycloalkyl groups can be fused or non-fused, monocyclic or polycyclic. Any suitable aryl, heteroaryl, cycloalkyl or heterocycloalkyl group can be used as $R_1$ and/or $R_2$ and /or $R_3$ and /or $R_3'$.

When the specified groups are substituted, the substituents may be selected from: halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O—($C_{1-6}$-alkyl); O-aryl, aryl; aryl-($C_{1-6}$-alkyl); $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. These substituents may optionally be further substituted with a substituent selected from those exemplified above. The $R_1$ and/or $R_2$ and/or $R_3$ and/or $R_3'$ groups can be unsubstituted or substituted with any desired substituent.

In one preferred embodiment of compounds of the Formula I, $R_1$ and $R_2$ are selected to be different aryl, heteroaryl, cycloalkyl, and heterocycloalkyl groups.

Particularly preferred $R_1$ moieties are unsubstituted and substituted aryl groups, more preferably, substituted and unsubstituted phenyl groups. Even more preferably, $R_1$ is unsubstituted phenyl or 2,6-difluorophenyl.

Particularly preferred $R_2$ moieties are unsubstituted and substituted aryl groups, such as an unsubstituted or substituted phenyl group. Especially preferred is a phenyl group substituted in the para position, e.g., by a substituent selected from carboxyl, amido, $SO_2NH_2$, heteroaryl and heterocycle groups; other exemplary substituents for a phenyl group include those of the examples described below. Other especially preferred $R_2$ moieties include 4-(1,4-piperzin-1-yl)-phenyl, 4-sulfonamidophenyl, and 4-methoxyphenyl.

Especially preferred compounds of the Formula II are those represented by Formula IIa in Table A set forth below.

In a preferred embodiment of the Formula II, at least one $R_3$ is a halogen, such as fluorine, chlorine, bromine or iodine, preferably in an ortho position. More preferably, one $R_3$ moiety is hydrogen and the other two $R_3$ groups, which are preferably in the ortho positions, are independently selected from fluorine and hydrogen.

Although a compound of the Formula I, II or IIa may exhibit the phenomenon of tautomerism, the formulas expressly depict only one of the possible tautomeric forms. It is therefore to be understood that the invention encompasses, and the formulas are intended to also represent, tautomeric forms of the depicted structures. Exemplary tautomers of Formula I are depicted below, where the hydrogens alternately reside on either nitrogen of the pyrazole ring (i.e., tautomers 1 and 4), and either on the thiazole ring, or out onto the substituent nitrogen (i.e., tautomers 1 and 3). Any of these tautomers allow hydrogen bonding in various patterns with kinases.

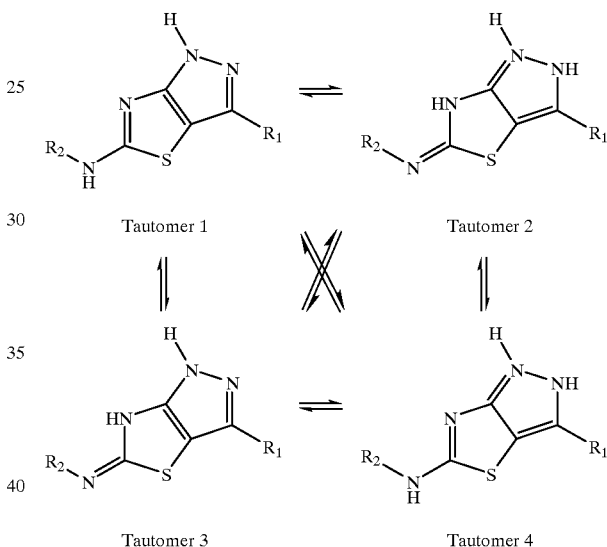

Tautomer 1    Tautomer 2

Tautomer 3    Tautomer 4

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the Formulas I, II or IIa are intended to cover solvated as well as unsolvated forms of the identified structures. For example, Formula I, II and IIa include compounds of the indicated structure in both hydrated and non-hydrated forms. Other examples of solvates include the structures in combination with isopropanol, ethanol, methanol, DMSO, ethyl acetate, acetic acid, or ethanolamine. Pharmaceutical compositions according to the invention comprise an active ingredient selected from compounds of the Formula I, II or IIa, pharmaceutically acceptable salts, multimeric forms, prodrugs, and pharmacologically active metabolites thereof, and pharmaceutically acceptable salts of such metabolites. Such compounds, salts, multimers, prodrugs, and metabolites are sometimes herein referred to collectively as "cell-cycle control agents."

The cell-cycle control agents of the invention inhibit the kinase activity of CDK/cyclin complexes, such as those active in the $G_0$ or $G_1$ stage of the cell cycle, e.g., CDK2, CDK4, and/or CDK6 complexes. In one preferred embodiment, cell-cycle control agents of the invention have an inhibition constant against CDK4 or a CDK4/D-type cyclin complex of about 5 $\mu$M or less, more preferably of about 1 $\mu$M or less, more preferably of about 500 nM or less, even more preferably of about 200 nM or less. In another preferred embodiment, the cell-cycle control agents have an inhibition constant against CDK2 or a CDK2/E-type cyclin complex of about 5 $\mu$M or less, more preferably of about 1 $\mu$M or less, more preferably of about 500 nM or less, even more preferably of about 200 nM or less, and further preferably of about 100 nM or less.

A "pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, or inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

The term "multimer" refers to multivalent or multimeric forms of active forms of the compounds of the Formula I. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding (see, for example, Lee et al., *Biochem.*, 1984, 23:4255). The artisan may control the multivalency and spacing by selection of a suitable carrier moiety or linker units. Useful moieties include molecular supports containing a multiplicity of functional groups that can be reacted with functional groups associated with the active compounds of the invention. A variety of carrier moieties may be used to build highly active multimers, including proteins such as BSA (bovine serum albumin) or HSA (human serum albumin), peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

The term "prodrug" refers to a metabolic precursor of a specified compound that may be inactive when administered to a subject but is converted under physiological conditions or by solvolysis to the specified compound or a pharmaceutically acceptable salt of such compound.

The term "active metabolite" is intended to mean a pharmacologically active product produced through metabolism in the body of a specified compound or salt thereof.

Prodrugs and active metabolites of compounds of the Formula I, II or IIa may be identified using routine techniques known in the art. See, e.g., Bertolini et al., *J. Med. Chem.*, 40, 2011–2016 (1997); Shan, et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); and Larsen, *Design and Application of Prodrugs*, Drug Design and Development (Krogsgaard-Larsen et al., eds., Harwood Academic Publishers, 1991).

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention.

Cell-cycle control agents in accordance with the invention are useful as pharmaceuticals for treating proliferative disorders in mammals, preferably humans, marked by unwanted proliferation of endogenous tissue. Compounds of the Formula I, II and IIa may be used for treating subjects having a disorder associated with excessive cell proliferation, e.g., cancers, psoriasis, immunological disorders involving undesired proliferation of leukocytes, and restenosis and other smooth-muscle disorders. Furthermore, such compounds may be used to prevent de-differentiation of post-mitotic tissue and/or cells.

Pharmaceutical compositions or preparations of the invention comprise a pharmaceutically acceptable carrier and an effective amount of at least one cell-cycle control agent. The specific dosage amount of a cell-cycle control agent being administered to obtain therapeutic or inhibitory effects may be determined in a manner known in the art according to the particular circumstances surrounding the case, including, e.g., the specific agent being administered, the route of administration, the condition being treated, and the subject or host being treated. An exemplary total daily dose of a cell-cycle control agent, which may be administered in single or multiple doses, contains a dosage level of from about 0.01 mg/kg body weight to about 50 mg/kg body weight.

The cell-cycle control agents of the invention may be administered by any of a variety of suitable routes, such as orally, rectally, transdermally, subcutaneously, intravenously, intramuscularly, or intranasally. The cell-cycle control agents are preferably formulated into compositions suitable for the desired routes before being administered.

A pharmaceutical composition or preparation according to the invention comprises an effective amount of a cell-cycle control agent and a pharmaceutically acceptable carrier, such as a diluent or excipient for the agent. When the carrier serves as a diluent, it may be a solid, semi-solid, or liquid material acting as a vehicle, excipient, or medium for the active ingredient(s). Compositions according to the invention may be made by admixing the active ingredient(s) with a carrier, or diluting it with a carrier, or enclosing or encapsulating it within a carrier, which may be in the form of a capsule, sachet, paper container, or the like. Exemplary ingredients, in addition to one or more cell-cycle control agents and any other active ingredients, include Avicel (microcrystalline cellulose), starch, lactose, calcium sulfate dihydrate, terra alba, sucrose, talc, gelatin, agar, pectin, acacia, magnesium stearate, stearic acid, peanut oil, olive oil, glyceryl monostearate, Tween 80 (polysorbate 80), 1,3-butanediol, cocoa butter, beeswax, polyethylene glycol, propylene glycol, sorbitan monostearate, polysorbate 60, 2-octyldodecanol, benzyl alcohol, glycine, sorbic acid, potassium sorbate, disodium hydrogen phosphate, sodium chloride, and water.

The compositions may be prepared in any of a variety of forms suitable for the desired mode of administration. For example, pharmaceutical compositions may be prepared in the form of tablets, pills, powders, lozenges, sachets, cachets, elixirs, suspensions, emulsions, solutions, syrups, aerosols (as solids or in liquid media), ointments (e.g., containing up to 10% by weight of a cell-cycle control agent), soft-gel and hard-gel capsules, suppositories, sterile injectable solutions, sterile packaged powders, and the like.

Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an agent is dissolved in an aqueous solution of an organic or inorganic acid, such as 0.3 M-solution of succinic acid or citric acid. If a soluble salt form is not available, the agent may be dissolved in a suitable cosolvent or combinations of cosolvents. Examples of suitable cosolvents include alcohol, propylene glycol, polyethylene glycol 300, polysorbate 80, glycerin and the like in concentrations ranging from 0–60% of the total volume. In an exemplary embodiment, a compound of Formula I, II or IIa is dissolved in DMSO and diluted with water. The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

The particular formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants are selected from those known in the art as appropriate to the barrier to be permeated.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be administered orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the agents according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a compound of the Formula I, II, or IIa is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and scelera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The agents may also be formulated in rectal compositions such as suppositories or retention enemas, e.g., containing conventional suppository bases such as cocoa butter or other glycerides.

In addition to the formulations described above, the agents may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration; the proportions of a co-solvent system may be varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid—or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

A pharmaceutical composition according to the invention may optionally comprise, in addition to a cell-cycle control agent, one or more other active ingredients, such as a known antiproliferative agent that is compatible with the cell-cycle control agent and suitable for the indication being treated.

The compounds are useful as anti-angiogenesis agents and as agents for modulating and/or inhibiting the activity of CDKs, thus providing treatments for cancer or other diseases associated with cellular proliferation mediated by protein kinases. The agents and compositions of the present invention are useful as inhibitors of mammalian CDK/cyclin complexes, insect CDK, or fungal CDK complexes. Such agents and compositions are also useful for controlling proliferation, differentiation, and/or apoptosis. Inhibition of CDKs can be useful to treat cancer, inflammation, cardiac disease state, and Alzheimer's.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more protein kinases. Thus, e.g., a therapeutically effective amount of an agent is a quantity sufficient to modulate, regulate, or inhibit the activity of one or more CDKs such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, and can be routinely determined by one skilled in the art. "Treating" is intended to mean at least the mitigation of a disease condition in a mammal, such as a human, that is effected, at least in part, by the activity of one or more protein kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The inventive agents may be prepared using the reaction routes and synthesis schemes as described below, employing the techniques available in the art using starting materials that are readily available. The preparation of exemplary compounds of the present invention is described in detail in the following examples, but the artisan will recognize that the chemical reactions described may be readily adapted to prepare a number of other protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

EXAMPLES

Materials and Methods

In the examples described below, unless otherwise indicated, all temperatures are set forth in degrees Celsius and all parts and percentages are by weight, unless indicated otherwise. Reagents were purchased from commercial suppliers such as Aldrich Chemical Company or Lancaster Synthesis Ltd. and were used without further purification unless otherwise indicated. Tetrahydrofuran (THF) and N,N-dimethylformamide (DMF) were purchased from Aldrich in Sure seal bottles and used as received. All solvents were purified using standard methods readily known to those skilled in the art, unless otherwise indicated.

The reactions set forth below were done generally under a positive pressure of nitrogen, argon, or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates from Analtech (0.25 mm) and eluted with the appropriate solvent ratios (v/v), and are denoted where appropriate. The reactions were assayed by TLC, NMR, or HPLC and terminated as judged by the consumption of starting material. Visualization of the TLC plates was done with a UV lamp, iodine, or p-anisaldehyde spray reagent or phosphomolybdic acid reagent (Aldrich Chemical 20 wt % in ethanol) and activated with heat.

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Merck EM flash silica gel (47–61 $\mu$m) and a silica gel:crude material ratio of about 20:1 to 50:1 unless otherwise stated. Hydrogenolysis was done at the pressure indicated in the examples or at ambient pressure.

$^1$H-NMR spectra were recorded on a Bruker instrument operating at 300 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). The mass spectra were obtained using LSIMS or electrospray. All melting points (mp) are uncorrected.

The starting materials used in the examples are commercially available or can be prepared using techniques generally known in the art.

Example A(1)

5-(4-Methoxyphenylamino)-3-phenyl-1H-pyrazolo[4,5-d]thiazole Hydrobromic Acid Salt. (Compound 1)

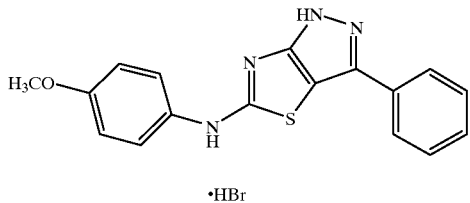

•HBr

A mixture of 5-amino-4-bromo-3-phenyl-pyrazole available from Lancaster Synthesis, Ltd. ("Lancaster"), (250 mg, 1.05 mmol) and 4-methoxyphenyl isothiocyanate available from Lancaster (191 mg, 1.15 mmol) in dioxane (10 mL) was heated at reflux for 18 hrs and then allowed to cool to ambient temperature. The solvent was removed under reduced pressure, and the resultant solid recrystallized from boiling ethanol to afford 250 mg (74% yield) of a yellow solid, mp 259° C. $^1$H NMR (DMSO-$d_6$): δ0.28 (1H, s), 7.68 (2H, bs), 7.66 (2H, d, J=2.4 Hz), 7.52 (2H, dd, J=7.9, 7.5 Hz), 7.37 (1H, dd, J=7.4, 7.3 Hz), 6.97 (2H, d, J=9.1 Hz), 3.72 (3H, s). IR (KBr): 3235, 3176, 1605, 1566, 1511, 1450, 1233 cm$^{-1}$. HRFABMS: Calcd. For $C_{17}H_{15}N_4OS$ (MH$^+$): 323.0967. Found: 323.0968. Anal. Calcd. for $C_{17}H_{14}N_4OS$·HBr· 0.7 EtOH: C, 50.74; H, 4.44; N, 12.86; S, 7.36. Found: C, 50.68; H, 4.64; N, 12.65; S, 7.24.

Example A(2)

3-Phenyl-5-(4-sulfonamidophenylamino)-1H-pyrazolo[4,5-d]thiazole Hydrobromic Acid Salt. (Compound 2)

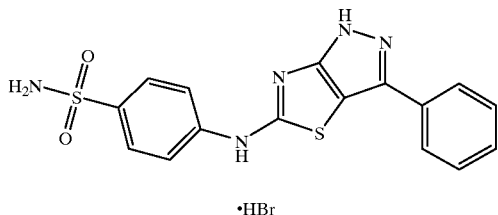

•HBr

The title compound was prepared in a manner analogous to that used in Example A(1). 5-Amino-4-bromo-3-phenyl-pyrazole available from Lancaster and 4-isothiocyanato-benzenesulfonamide available from Lancaster provided a cream-colored amorphous solid in 89% yield, mp>300° C. $^1$H NMR (DMSO-$d_6$): δ8.09 (2H, d, J=8.9 Hz), 7.99 (2H, d, J=8.6 Hz), 7.85 (2H, d, J=7.3 Hz), 7.70 (2H, dd, J=7.8, 7.5 Hz), 7.55 (1H, t, J=7.4, 7.3 Hz), 6.00 (2H, bs). IR (KBr): 3243, 3174, 3095, 3035, 2986, 2886, 2748, 1616, 1596, 1506, 1467 cm$^{-1}$. HRFABMS: Calcd. for $C_{16}H_{14}N_5O_2S_2$ (MH$^+$): 372.0589. Found: 372.0592. Anal. Calcd. for $C_{16}H_{13}N_5O_2S_2$·HBr· 0.2 EtOH: C, 42.68; H, 3.32; N, 15.17; S, 13.89. Found: C, 42.62; H, 3.17; N, 15.10; S, 13.54.

Example B(1)

5-[4-(4-Methyl-piperazin-1-yl)-phenylamino]-3-phenyl-1H-pyrazolo[4,5-d]thiazole Hydrobromic Acid Salt. (Compound 4)

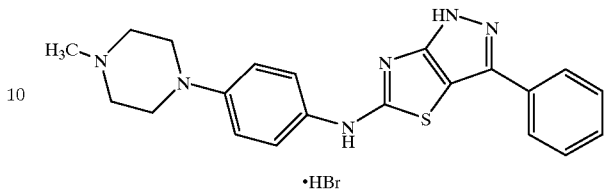

•HBr

1-[4-(4-Methyl-piperazin-1-yl)-phenyl]-3-(3-phenyl-pyrazol-5-yl)-thiourea, which has structural formula

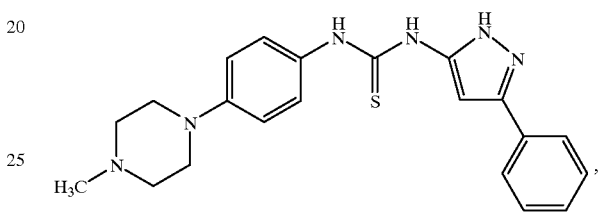

was first prepared as follows. A mixture of 5-amino-3-phenyl-pyrazole available from Lancaster (362 mg, 2.27 mmol) and 1-(4-isothiocyanato-phenyl)-4-methyl-piperazine (prepared as in Chong et al., International Publication No. WO 99/21845 (1999) incorporated by reference in its entirety); 500 mg, 2.27 mmol) in dioxane (10 mL) was heated at reflux for 4 hrs, then allowed to cool to ambient temperature. The resultant solid was collected by filtration, rinsed with cold dioxane, and dried under vacuum to furnish a cream-colored solid, 800 mg (90% yield), which was used without further purification. $^1$H NMR (DMSO-$d_6$): δ13.10 (1H, bs), 11.48 (1H, bs), 10.68 (1H, bs), 7.72 (2H, d, J=7.2 Hz), 7.37–7.52 (5H, m), 6.93 (2H, d, J=9.0 Hz), 6.38 (1H, s), 3.15 (4H, dd, J=5.0, 4.5 Hz), 2.24 (3H, s).

The title compound was prepared following a procedure of Eilingsfeld, H., German Patent Publication DE 2429195 (Jun. 18, 1974), incorporated by reference herein in its entirety. To a suspension of 1-[4-(4-methyl-piperazin-1-yl)-phenyl]-3-(3-phenyl-pyrazol-5-yl)-thiourea (250 mg, 0.64 mmol) in glacial acetic acid (2 mL) was added a solution of 1.5M Br$_2$ in glacial acetic acid (467 μL, 0.70 mmol). The resultant mixture was heated to 80° C. for 3 hrs, allowed to cool to ambient temperature, and diluted with H$_2$O. The solid was collected by filtration, rinsed with H$_2$O, and dried under vacuum to furnish a white solid, 60 mg (24% yield), mp 220–222° C. $^1$H NMR (CD$_3$OD): δ7.57 (4H, bd, J=8.7 Hz), 7.38 (2H, dd, J=8.0, 7.2 Hz), 7.28 (1H, dd, J=7.4, 7.2 Hz), 6.95 (2H, d, J=9.0 Hz), 3.28 (4H, bs), 2.82 (3H, s). HRFABMS: Calcd. for $C_{21}H_{23}N_6S$ (MH$^+$): 391.1705. Found: 391.1692. Anal. Calcd. for $C_{21}H_{22}N_6S$·HBr·1.5 H$_2$O: C, 50.60; H, 5.26; N, 16.86; S, 6.46. Found: C, 50.65; H, 5.05; N, 16.99; S, 6.64.

Example C(1)

3-(2,6-Difluorophenyl)-5-(4-sulfonamidophenylamino)-1H-pyrazolo [4,5-d] thiazole. (Compound 3)

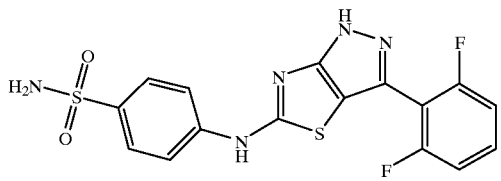

3-(2,6-Difluoro-phenyl)-3-oxo-propionitrile, which has structural formula

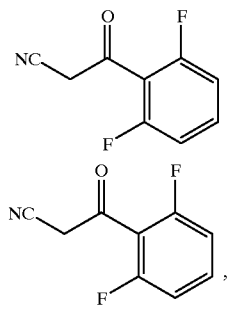

was first prepared as follows. According to procedure of Sjogren et al., *J. Med. Chem.* vol. 34 (1991), pp. 3295–3301, incorporated herein by reference, to a stirred −78° C. solution of acetonitrile (from Aldrich Chemical, 2.15 mL, 41.2 mmol) in THF (50 mL) was added over 5 min a solution of 2.5 M n-BuLi in hexane (12.4 mL, 30.9 mmol). The resultant slurry was stirred at −78° C. for half hour and then treated over 5 min with 2,6-difluoro-benzoyl chloride from Aldrich Chemical (2.17 g, 10.4 mmol). After 45 min, the reaction mixture was quenched with sat. aq. $NH_4Cl$ (25 mL), and partitioned between 1N HCl and EtOAc. The organic layer was separated, washed with brine, dried over $Na_2SO_4$, filtered, and concentrated to give a brown oil, which was purified via column chromatography with 10% MeOH/$CH_2Cl_2$ as eluant to furnish a brown oil, 1.83 g (82% yield) that was used without further purification. $^1$H NMR ($CDCl_3$): δ7.40 (3H, s), 3.92 (2H, s). IR: 2913, 2265, 2216, 1732, 1562, 1432 cm$^{-1}$.

5-Amino-3-(2,6-difluoro-phenyl)-pyrazole, which has structural formula

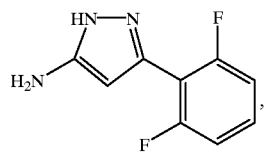

was then prepared as follows. A mixture of crude 3-(2,6-difluoro-phenyl)-3-oxo-propionitrile (500 mg, 2.76 mmol) and hydrazine hydrate (803 μL, 16.6 mmol) in absolute ethanol (5 mL) was heated at reflux for 18 hrs. The mixture was allowed to cool to ambient temperature and solvent removed to give a brown wax, which was purified via column chromatography with 5% MeOH/$CH_2Cl_2$ as eluant to furnish a brown semi-solid, 300 mg (56% yield), that typically was used without any further purification. $^1$H NMR ($CD_3OD$): δ7.30–7.39 (1H, m), 7.08 (2H, dd, J=8.6, 8.5 Hz), 5.98 (1H, bs). IR: 3306, 1624, 1586, 1511 cm$^{-1}$. FABMS (MH$^+$): 196.

4-{3-[3-(2,6-Difluoro-phenyl)-pyrazol-5-yl]-thioureido}-benzenesulfonamide, which has structural formula

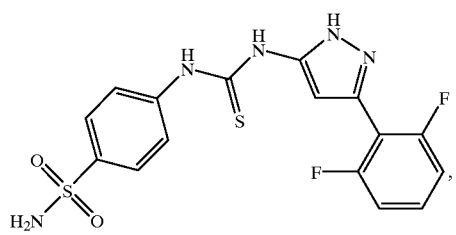

was prepared in a manner analogous to 1-[4-(4-methyl-piperazin-1-yl)-phenyl]-3-(3-phenyl-pyrazol-5-yl)-thiourea for Example B(1), from 5-amino-3-(2,6-difluoro-phenyl)-pyrazole and 4-isothiocyanato-benzenesulfonamide, to provide a yellow powder in 64% yield, which was used without further purification. $^1$H NMR (DMSO-$d_6$): δ10.78 (1H, s), 7.68 (2H, d, J=8.8 Hz), 7.59 (2H, d, J=8.8 Hz),7.28–7.39 (1H, m), 7.13 (2H, s), 7.08 (2H, dd, J=8.6, 8.5 Hz), 6.25 (1H, bs). IR (KBr): 3321, 3243, 3086, 2977, 2859, 1655, 1598, 1560, 1500, 1174 cm$^{-1}$.

The title compound was prepared in a manner like that described for Example B(1) from 4-{3-[3-(2,6-difluoro-phenyl)-pyrazol-5-yl]-thioureido}-benzene sulfonamide to give a crude product which recrystallized from ethylene glycol to furnish a cream-colored solid in 21% yield. 1H NMR (DMSO-$d_6$): δ13.12 (1H, s), 10.88 (1H, s), 7.90 (2H, d, J=8.0 Hz), 7.81 (2H, d, J=8.9 Hz), 7.48–7.59 (1H, m), 7.27–7.38 (2H, m), 7.24 (2H, s). IR (KBr): 3448, 3312, 3239, 3058, 1628, 1604, 1551, 1490, 1154 cm$^{31\ 1}$. HRFABMS: Calcd. for $C_{16}H_{11}F_2N_5O_2S_2Na$ (MNa$^+$): 430.0220. Found: 430.0229. Anal. Calcd. for Calcd. for $C_{16}H_{11}F_2N_5O_2S_2$.0.4 $H_2O$: C, 46.35; H, 2.87; N, 16.89; S, 15.47. Found: C, 46.44; H, 2.74; N, 16.57; S, 15.34.

Example C(2)

3-(2,6-Difluoro-phenyl)-5-[(4-methyl-piperazin-1-yl)-phenylamino]-1H-pyrazolo [4,5-d]thiazole. (Compound 5)

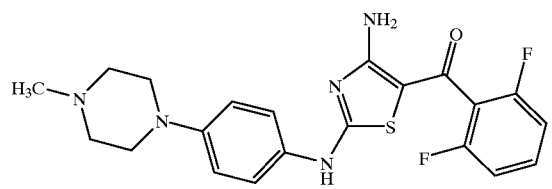

1-[3-(2,6-Difluoro-phenyl)-pyrazol-5-yl ]-3-[4-(4-methyl-piperazin-1-yl)-phenyl]-thiourea, which has structural formula

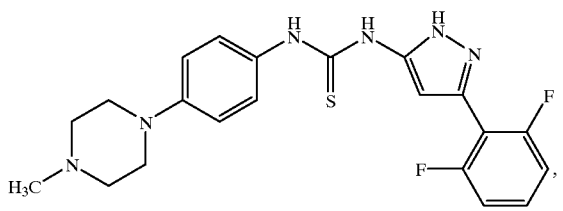

was prepared in a manner analogous to 1-[4-(4-methyl-piperazin-1-yl)-phenyl ]-3-(3-phenyl-pyrazol-5-yl)-thiourea for Example B(1), from 5-amino-3-(2,6-difluoro-phenyl)-pyrazole (from Example C(1) and 1-(4-isothiocyanato-phenyl)-4-methyl-piperazine, to provide a white solid in 31% yield, which was used without further purification. $^1$H NMR (DMSO-d$_6$): δ12.82 (1H, s), 11.18 (1H, bs), 10.52 (1H, s), 7.30–7.42 (1H, m), 7.26 (2H, d, J=8.9 Hz), 7.10 (2H, dd, J=8.6, 8.5 Hz), 6.82 (2H, d, J=9.0 Hz), 6.24 (1H, s), 3.22 (4H, s), 2.42 (4H, s), 2.58 (3H, s).

The title compound was prepared in a manner like that described for Example B(1) from 1-[3-(2,6-difluoro-phenyl)-pyrazol-5-yl ]-3-[4-(4-methyl-piperazin-1-yl)-phenyl]-thiourea to give a crude product that was purified via column chromatography with 5% MeOH/CH$_2$Cl$_2$ as eluant to furnish a pale yellow solid in 29% yield, mp 208–210° C. $^1$H NMR (CD$_3$OD): δ7.91 (1H, s), 7.58 (2H, d, J=9.0 Hz), 7.40–7.52 (1H, m), 7.17 (2H, dd, J=8.4, 7.8 Hz), 7.02 (2H, d, J=9.0 Hz), 3.21 (4H, dd, J=5.3, 4.6 Hz), 2.67 (4H, dd, J=5.1, 4.8 Hz), 2.38 (3H, s). HRFABMS: Calcd. for C$_{21}$H$_{21}$F$_2$N$_6$S (MH$^+$): 427.1516. Found: 427.1505. Anal. Calcd. for Calcd. for C$_{21}$H$_{20}$F$_2$N$_6$S. 0.2 MeOH. 0.CHCl$_3$: C, 56.27; H, 4.63; N, 18.40; S, 7.02. Found: C, 56.42; H, 4.77; N, 18.21; S, 6.84.

The exemplary compounds described above may be tested for their activity as described below. The ability of a protein kinase inhibitor to block cellular proliferation induced by growth factors is directly correlated with its ability to block receptor autophosphorylation. To measure the protein kinase inhibition activity of the compounds, the following experimental conditions were employed.

Biochemical And Biological Evaluation

Cyclin-dependent kinase activity was measured by quantifying the enzyme-catalyzed, time-dependent incorporation of radioactive phosphate from [$^{32}$P]ATP or [$^{33}$P]ATP into a protein substrate. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4), 10 mM MgCl$_2$, 25 μM adenosine triphosphate (ATP), 1 mg/mL ovalbumin, 5 μg/mL leupeptin, 1 mM dithiothreitol, 10 mM β glycerophosphate, 0.1 mM sodium vanadate, 1 mM sodium fluoride, 2.5 mM ethylene glycol-bis(β-aminoethyl ether)-N,N,N'N'-tetraacetic acid (EGTA), 2% (v/v) dimethylsulfoxide, and 0.03–0.4 μCi [$^{32/33}$P]ATP per reaction. Reactions were initiated with enzyme, incubated at 30° C., and terminated after 20 minutes by the addition of ethylenediaminetetraacetic acid (EDTA) to 250 mM. The phosphorylated substrate was then captured on a nitrocellulose or phosphocellulose membrane using a 96-well filtration manifold, and unincorporated radioactivity was removed by repeated washing with 0.85% phosphoric acid. Radioactivity was quantified by exposing the dried membranes to a phosphorimager.

Apparent K$_i$ values were measured by assaying enzyme activity in the presence of different inhibitor compound concentrations and subtracting the background radioactivity measured in the absence of enzyme.

Inhibition of CDK4/Cyclin D Retinoblastoma Kinase Activity

A complex of human CDK4 and cyclin D3, or a complex of human CDK4 and genetically truncated (1–264) cyclin D3, was purified using traditional biochemical chromatographic techniques from insect cells that had been co-infected with the corresponding baculovirus expression vectors (see e.g., Meijer and Kim, "Chemical Inhibitors of Cyclin-Dependent Kinases," Methods in Enzymol,. vol. 283 (1997), pp. 113–128.). The enzyme complex (5 or 50 nM) was assayed with 0.3–0.5 μg of purified recombinant retinoblastoma protein fragment (Rb) as a substrate. The engineered Rb fragment (residues 386–928 of the native retinoblastoma protein; 62.3 kDa) contains the majority of the phosphorylation sites found in the native 106-kDa protein, as well as a tag of six histidine residues for ease of purification. Phosphorylated Rb substrate was captured by microfiltration on a nitrocellulose membrane and quantified using a phosphorimager as described above. For measurement of tight-binding inhibitors, the enzyme complex concentration was lowered to 5 nM, and the assay duration was extended to 60 minutes, during which the time-dependence of product formation was linear.

Inhibition of CDK2/Cyclin A Retinoblastoma Kinase Activity

CDK2 was purified using published methodology (Rosenblatt et al., "Purification and Crystallization of Human Cyclin-dependent Kinase 2," J. Mol. Biol., vol. 230, 1993, pp. 1317–1319) from insect cells that had been infected with a baculovirus expression vector. Cyclin A was purified from E. coli cells expressing full-length recombinant cyclin A, and a truncated cyclin A construct was generated by limited proteolysis and purified as described previously (Jeffrey et al., "Mechanism of CDK activation revealed by the structure of a cyclin A-CDK2 complex," Nature, vol. 376 (Jul. 27, 1995), pp. 313–320). A complex of CDK2 and proteolyzed cyclin A was prepared and purified by gel filtration. The substrate for this assay was the same Rb substrate fragment used for the CDK4 assays, and the methodology of the CDK2/cyclin A and the CDK4/cyclin D3 assays was essentially the same, except that CDK2 was present at 150 nM or 10 nM. K$_i$ values were measured as described above.

Results of assays performed on compounds, which include the specific examples described above are provided below in Table A. Unless indicated otherwise in a particular entry, the units and assays used are as indicated in the applicable column of the table.

TABLE A

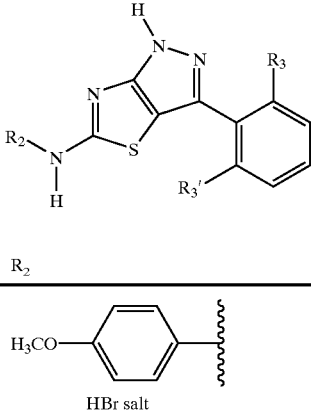

(IIa)

| Compound | R₂ | R₃' | R₃ | Ki CDK4/D3 (nM) | Ki CDK2/A (nM) | IC50 HCT116 (μM) |
|---|---|---|---|---|---|---|
| 1 | 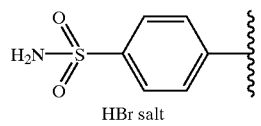 H₃CO-C₆H₄- HBr salt | H | H | 1600 | 1000 | N.D. |
| 2 | H₂N-SO₂-C₆H₄- HBr salt | H | H | 390 | 34 | >25 |
| 3 | H₂N-SO₂-C₆H₄- | F | F | 18% @ 1 μm | 41% @ 1 μm | 16% @ 25 μm |
| 4 | H₃C-piperazinyl-C₆H₄- HBr salt | H | H | 170 | 1600 | N.D. |
| 5 | H₃C-piperazinyl-C₆H₄- | F | F | 29% @ 1 μm | 17% @ 1 μm | N.D. |

Note:
N.D. = no data.

Inhibition of Cell Growth: Assessment of Cytotoxicity

Inhibition of cell growth was measured using the tetrazolium salt assay, which is based on the ability of viable cells to reduce 3-(4,5-dimethylthiazol-2-yl)-2,5-[2H]-diphenyltetrazolium bromide (MTT) to formazan (Mossman, *Journal of Immunological Methods*, vol. 65 (1983), pp. 55–58). The water-insoluble purple formazan product was then detected spectrophotometrically. The HCT 116 cell line was grown in 96-well plates. Cells were plated in the appropriate medium at a volume of 135 μl/well in McCoy's 5A Medium. Plates were incubated for four hours before addition of inhibitor compounds. Different concentrations of inhibitor compounds were added in 0.5% (v/v) dimethylsulfoxide (15 μL/well), and cells were incubated at 37° C. (5% CO₂) for four to six days (depending on cell type). At the end of the incubation, MTT was added to a final concentration of 0.2 mg/mL, and cells were incubated for 4 hours more at 37° C. After centrifugation of the plates and removal of medium, the absorbence of the formazan (solubilized in dimethylsulfoxide) was measured at 540 nm. The concentration of inhibitor compound causing 50% inhibition of growth was determined from the linear portion of a semi-log plot of inhibitor concentration versus percentage inhibition. All results were compared to control cells treated only with 0.5% (v/v) dimethylsulfoxide.

The examples above illustrate compounds according to the Formula I, II and IIa and assays that may readily be performed to determine their activity levels against the various CDK/cyclin complexes. It will be apparent that such assays or other suitable assays known in the art may be used to select an inhibitor having a desired level of activity against a selected target.

The exemplary compounds described above may be formulated into pharmaceutical compositions according to the following general examples.

Example of Parenteral Composition

To prepare a parenteral pharmaceutical composition suitable for administration by injection, 100 mg of a water-soluble salt of a compound of Formula I, II, or IIa is dissolved in DMSO and then mixed with 10 mL of 0.9% sterile saline. The mixture is incorporated into a dosage unit form suitable for administration by injection.

Example of Oral Composition

To prepare a pharmaceutical composition for oral delivery, 100 mg of a compound of Formula I, II, or IIa is mixed with 750 mg of lactose. The mixture is incorporated into an oral dosage unit for, such as a hard gelatin capsule, which is suitable for oral administration.

The invention has been illustrated by reference to specific examples and preferred embodiments. It should be understood that the invention is intended not to be limited by the foregoing description, but to be defined by the appended claims and their equivalents.

What is claimed is:

1. A compound of the Formula I:

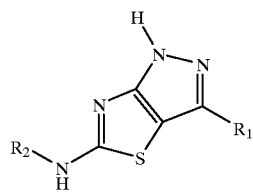

(I)

wherein:

R₁ is a group selected from substituted and unsubstituted ethyl, n-propyl, isopropyl, butyl, isobutyl, sec-butyl, tert-butyl, pentyl, tert-pentyl, hexyl, isohexyl, aryl, heteroaryl, cycloalkyl, and heterocycloalkyl groups; and R₂ is a group selected from substituted and unsubstituted alkyl, aryl, heteroaryl, cycloalkyl, and heterocycloalkyl groups, with the proviso that R₁ and R₂ may not both be an unsubstituted phenyl;

or a pharmaceutically acceptable salt or a prodrug.

2. A compound, salt, or prodrug according to claim 1, wherein R₁ is a substituted or unsubstituted aryl or heteroaryl group, and R₂ is a substituted or unsubstituted aryl or heteroaryl group.

3. A compound, salt, or prodrug according to claim 1, wherein R₁ is a substituted or unsubstituted phenyl group, and R₂ is a phenyl group substituted in the para position.

4. A compound having a structure selected from the group consisting of:

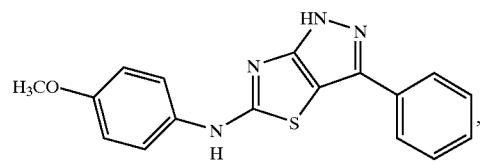

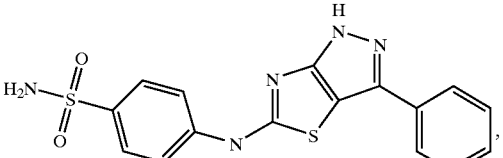

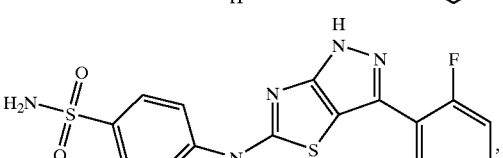

and

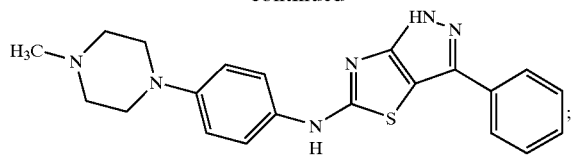

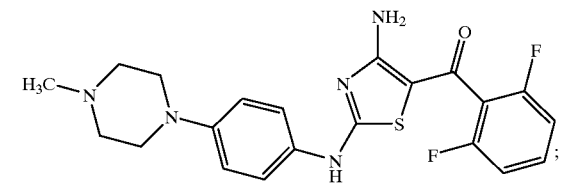

or a pharmaceutically acceptable salt or a prodrug.

5. A compound of the Formula II:

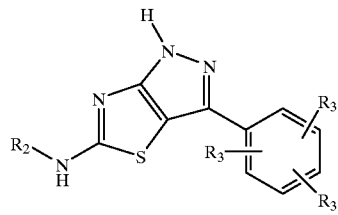

(II)

wherein:

R₂ is a substituted or unsubstituted alkyl, aryl, heteroaryl, cycloalkyl, or heterocycloalkyl group; and each R₃ is independently hydrogen or halogen, or a substituted or unsubstituted alkyl, aryl, heteroaryl, cycloalkyl, or heterocycloalkyl group, with the proviso that if R₂ is an unsubstituted phenyl then all R₃ may not be hydrogen;

or a pharmaceutically acceptable salt or a prodrug.

6. A compound of the Formula IIa:

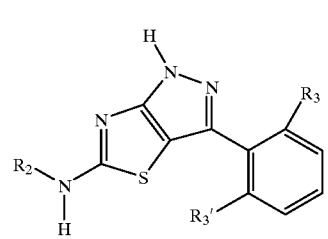

(IIa)

wherein:

R₂ is a substituted or unsubstituted alkyl, aryl, heteroaryl, cycloalkyl, or heterocycloalkyl group; and R₃ and R₃' are each independently hydrogen or halogen, or a substituted or unsubstituted alkyl, aryl, heteroaryl, cycloalkyl, or heterocycloalkyl group, with the proviso that if R₂ is an unsubstituted phenyl then R₃ and R₃' may not both be hydrogen;

or a pharmaceutically acceptable salt or a prodrug.

7. A pharmaceutical composition comprising:

(a) an amount of a cell-cycle control agent effective to inhibit CDK4 or a CDK4/cyclin complex, said cell-cycle control agent being selected from the group consisting of compounds of Formula I:

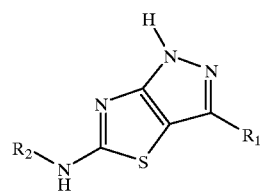

(I)

wherein:

R₁ is a group selected from substituted and unsubstituted ethyl, n-propyl, isopropyl, butyl, isobutyl, sec-butyl, tert-butyl, pentyl, tert-pentyl, hexyl, isohexyl, aryl, heteroaryl, cycloalkyl, and heterocycloalkyl groups; and R₂ is a group selected from substituted and unsubstituted alkyl, aryl, heteroaryl, cycloalkyl, and heterocycloalkyl groups;

pharmaceutically acceptable salts thereof; and (b) pharmaceutically acceptable carrier.

8. A pharmaceutical composition comprising:

(a) a therapeutically effective amount of a compound as defined in claim 1, a pharmaceutically acceptable salt, or a prodrug; and (b) a pharmaceutically acceptable carrier, diluent, vehicle or excipient therefor.

9. A pharmaceutical composition comprising:

(a) an effective amount for inhibiting a CDK or a CDK/cyclin complex of a cell-cycle control agent selected from:

(1) compounds of the Formula I:

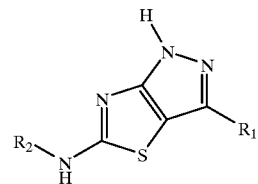

(I)

wherein:

R₁ is a group selected from substituted and unsubstituted ethyl, n-propyl, isopropyl, butyl, isobutyl, sec-butyl, tert-butyl, pentyl, tert-pentyl, hexyl, isohexyl, aryl, heteroaryl, cycloalkyl, and heterocycloalkyl groups; and R₂ is a group selected from substituted and unsubstituted alkyl, aryl, heteroaryl, cycloalkyl, and heterocycloalkyl groups; and (2) pharmaceutically acceptable salts of said compounds; and (b) a pharmaceutically acceptable carrier.

\* \* \* \* \*